United States Patent [19]

Aubrey

[11] Patent Number: 4,820,221
[45] Date of Patent: Apr. 11, 1989

[54] UPPER BODY BUOYANT GARMENT WITH IMPLANTED POSITIVE LUMBAR SUPPORT STRUCTURE

[76] Inventor: Martin G. Aubrey, 1307 Rothes Rd., Cary, N.C. 27511

[21] Appl. No.: 170,986

[22] Filed: Mar. 21, 1988

[51] Int. Cl.⁴ ............................. A16F 5/02; B63C 9/08
[52] U.S. Cl. .................................... 441/106; 441/108; 128/78
[58] Field of Search ................ 441/80, 88, 106, 108, 441/111, 112, 114, 115, 116, 129; 114/315; 440/6; 2/44, 2.5, 2.1 R; 128/78

[56] References Cited

U.S. PATENT DOCUMENTS

| | | | |
|---|---|---|---|
| 2,181,689 | 11/1939 | Bell | 2/44 |
| 2,730,096 | 1/1956 | Pease | 2/44 |
| 3,398,406 | 8/1968 | Waterbury | 2/2.5 |
| 3,449,778 | 6/1969 | Jones | 441/112 |
| 3,545,017 | 12/1970 | Cohn | 441/112 |
| 3,717,143 | 2/1973 | Johnson | 128/78 |
| 4,175,553 | 11/1979 | Rosenberg | 2/44 |

Primary Examiner—Joseph F. Peters, Jr.
Assistant Examiner—Edwin L. Swinehart
Attorney, Agent, or Firm—Rhodes, Coats & Bennett

[57] ABSTRACT

The present invention relates to a back or lumbar supporting buoyant outfit worn about the torso of a wearer. The back supporting buoyant outfit is comprised of a pliable, buoyant garment with a relatively firm back support structure implanted within the said buoyant garment. The back support structure aids the wearer in maintaining proper posture by hindering the wearer from bending his back incorrectly or excessively, while the buoyant garment provides buoyancy to the wearer.

3 Claims, 2 Drawing Sheets

UPPER BODY BUOYANT GARMENT WITH IMPLANTED POSITIVE LUMBAR SUPPORT STRUCTURE

FIELD OF THE INVENTION

The present invention relates to a theraputic device for the back and more particularly to a buoyant torso garment having a positive lumbar or back support structure implanted therein.

BACKGROUND OF THE INVENTION

There is perhaps no other type of pain any more agonizing and dehabilitating than the pain associated with back injuries or abnormalities associated with the back, spinal area, and lumbar area. As already eluded to, the pain associated with such injuries or conditions is often both persistent and tremendous. But of equal concern is the dehabilitating nature of such back conditions. An individual suffering from such often assumes a lifestyle that reflects an abstention from rigorous or even moderate exercise. Such individuals continue to live a life where they repeatedly withdraw from situations involving physical activity and exercise. Obviously, that is not a healthy approach, contributing to the back problem, inasmuch as exercise provides an opportunity to strengthen muscles, particularly back muscles which in turn can have a theraputic effect. In short, constructive exercise can go a long way toward correcting back problems.

It is widely accepted that swimming and water exercise in general is one of the most effective and efficient forms of exercise available. Not only does water exercise give the aerobic results desired, but such exercise tends to tone, firm and strengthen muscle groups, including back muscles, throughout the body.

Again, however, those individuals having back problems tend to avoid swimming and water sports such as water-skiing. There are a number of reasons for this. First and foremost, there is the pain associated with the back injury or condition that is brought to focus by swimming or any other exercise in the water. But other water sports such as water-skiing places a very substantial stress on the body and the back. Consequently, it makes sense for an individual with a back injury or problem participating in a water sport to wear some form of back support.

Therefore, there is a distinct need for a buoyant garment that will not only provide buoyancy for an individual but which will also provide positive back and lumbar support. Not only would such a buoyant garment that incorporates positive lumbar or back support structure enable people with back problems to be active in water environments, but such could also be used as a theraputic device for people with back problems.

SUMMARY AND OBJECTS OF THE INVENTION

The back supporting buoyant outfit of the present invention is worn about the torso of a wearer and includes a pliable, buoyant garment and a relatively firm, integral back support structure implanted witin the buoyant garment.

The buoyant garment is constructed of a buoyant material having the necessary buoyancy characteristics to safely support the wearer in the water.

The back support structure, implanted within the buoyant garment and preferably constructed of a firm plastic or rubber material, provides the wearer with positive back support to aid the wearer in maintaining proper posture by hindering the wearer from bending the lumbar region of his back incorrectly and hence straining the back. The implanted back support structure includes an upper transverse member located horizontally along the upper torso of the wearer and under the armpits of the wearer, a lower transverse member located horizontally along the lower back and hip area of the wearer, verticle side members attached between the upper transverse member and the lower transverse member and located at the wearer's sides, and a pair of verticle back members extending between the upper transverse member and the lower transverse member and located such that they extend along opposite sides of the spine.

In order to provide maximum protection and support to the wearer's back, the back supporting buoyant outfit must be closely fitted about the contour of the wearer's torso. The back supporting buoyant outfit may be form fitted or provided in varying sizes for different size individuals. In addition, the back supporting buoyant outfit includes adjusting straps and strap connectors for pulling and connecting the back supporting buoyant outfit tightly about the wearer's torso. This enables the back support structure to be tensioned and secured about the wearer such that a contoured and firm fit is achieved.

It is an object of the present invention to provide a theraputic exercise outfit designed to enable individuals who have back injuries or back abnormalities to exercise within a water environment.

Still a further object of the present invention resides in the provision of providing a lumbar support structure integral with a buoyant garment that includes means for tensioning the garment around a wearer's body such that the integral lumbar support structure is pulled into a relatively firm supporting relationship about the wearer's back.

Still a further object of the present invention resides in the provision of a upper body buoyant garment with an integral and implanted lumbar support structure that is comfortable, easy to adjust, and which is relatively simple in design and construction.

Still a further object of the present invention is to provide a back supporting buoyant outfit with sufficient buoyancy to safely support a wearer in the water.

Another object of the present invention is to provide a back supporting buoyant outfit which provides a wearer with an implanted back support structure.

Another object of the present invention is to provide a buoyant back support structure that will substantially reduce inhibitions that individuals with back problems and abnormalities may have relative to water and water related activities, and which will in fact encourage those individuals to exercise in the water for theraputic value as well as for fun.

Another object of the present invention is to provide a durable back supporting buoyant outfit which can withstand the stresses placed upon it by a wearer engaged in a water sport.

Other objects and advantages of the present invention will become apparent and obvious from a study of the following description and the accompanying drawings which are merely illustrative of such invention.

DETAILED DESCRIPTION OF THE INVENTION

Figure 1:
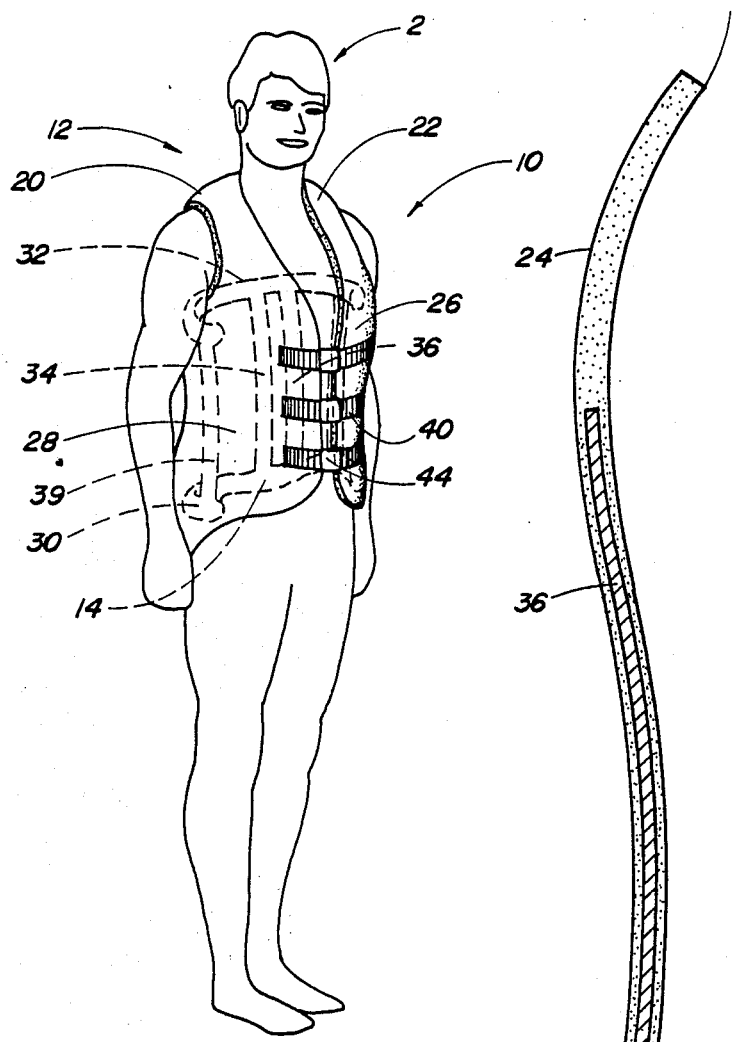
FIG. 1 is a perspective view of the back supporting buoyant outfit of the present invention worn about the torso of a wearer.

Referring now to the drawings, the back supporting buoyant outfit of the present invention, generally designated 10, is shown therein. As shown in FIG. 1, the back supporting buoyant outfit 10 includes a buoyant garment 12 with an implanted back support structure 14. The back supporting buoyant outfit 10 is worn about the upper body of a subject or wearer 2.

The buoyant garment 12 is made of a soft and pliable rubber material of sufficient buoyancy to support the wearer 2 in the water and durability to withstand the normal stresses placed upon it by the wearer 2 participating in water sports. The buoyant garment 12, designed to enclose the back supporting structure 14 and to provide buoyancy to the wearer 2, includes shoulder panels 20 and 22, back panel 24, and front panels 26 and 28. As shown in FIG. 1, the shoulder panels 20 and 22 extend over the shoulders of the wearer 2 forming a neck opening and arm openings in the buoyant garment 12. The neck opening and arm openings provide the wearer 2 with minimal hindrance for freedom of arm and neck movement. The back panel 24 follows the contour of the back of the wearer 2 and extends from his or her upper back downward to the area of his or her lower back adjacent to the sacrum. The front panels 26 and 28 open in the front of the wearer 2 to provide the wearer 2 with convenient adjustment of the buoyant garment 12 about his body.

In the drawings and in the above description, the buoyant garment 12 is shown in the form of a conventional ski vest. It is contemplated that a ski vest design may be one desirable embodiment of the buoyant garment 12. Although various buoyant materials may be utilized, it is contemplated that the ski vest type buoyant garment would be constructed of relatively pliable but resilient rubber material that is conventionally used in ski vest construction. It should be emphasized that the buoyant garment 12 can take on other particular designs and shapes. Essentially, an important feature of the present invention resides in the provision of a buoyant garment 12 that encircles a substantial area of a subject's back. Again, the particular design and shape of that garment might vary depending upon certain applications.

Figure 2:
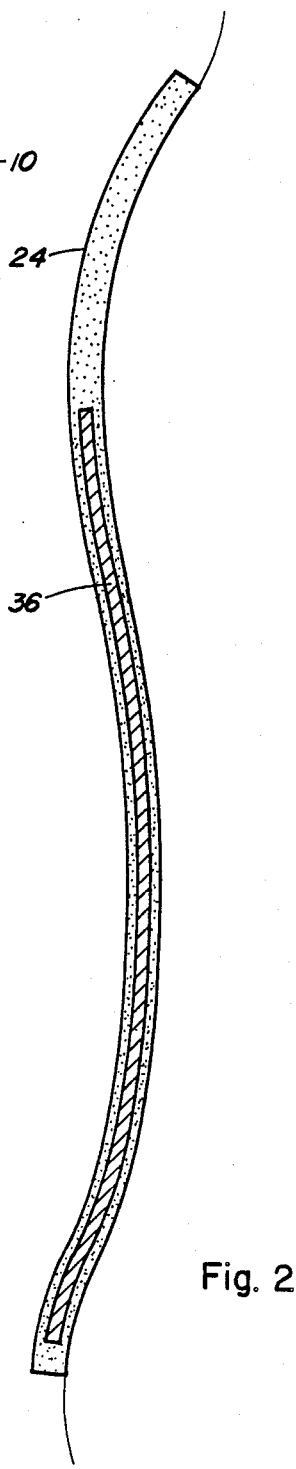
FIG. 2 is a verticle cross-sectional view taken along the lines 2—2 of FIG. 3.
Figure 3:
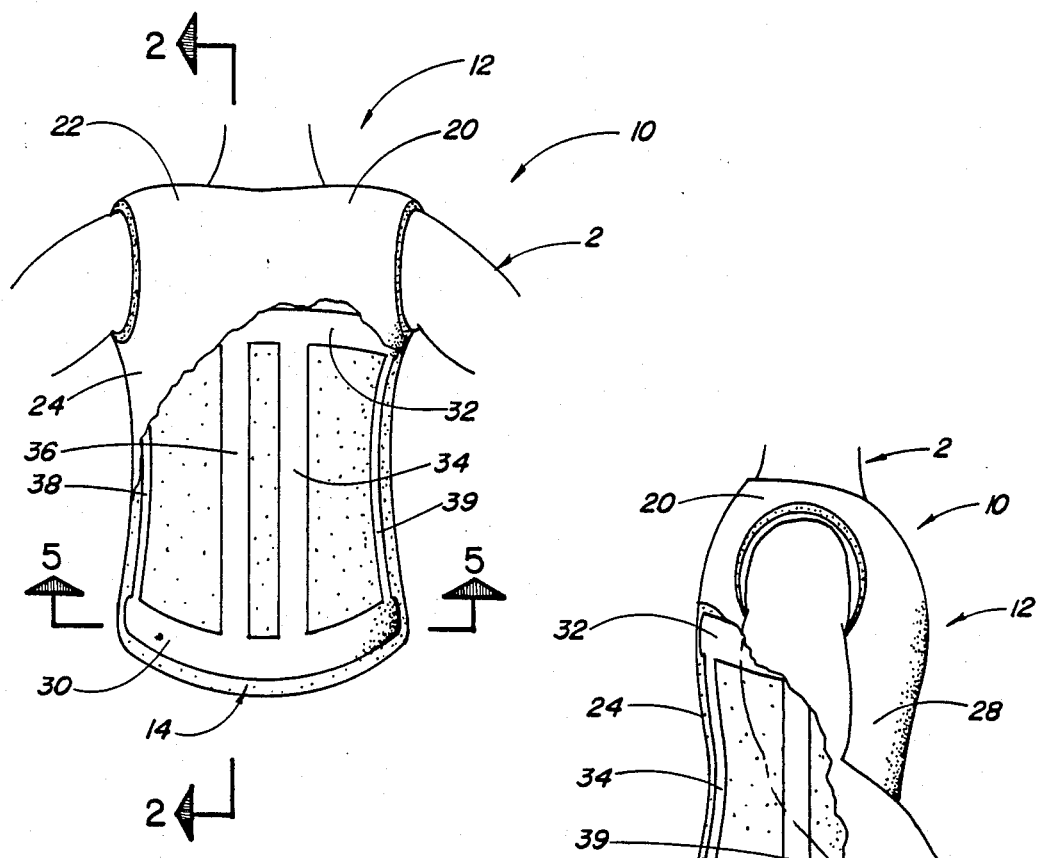
FIG. 3 is a back fragmentary view of the back supporting buoyant outfit of the present invention worn about the torso of a wearer.
Figure 4:
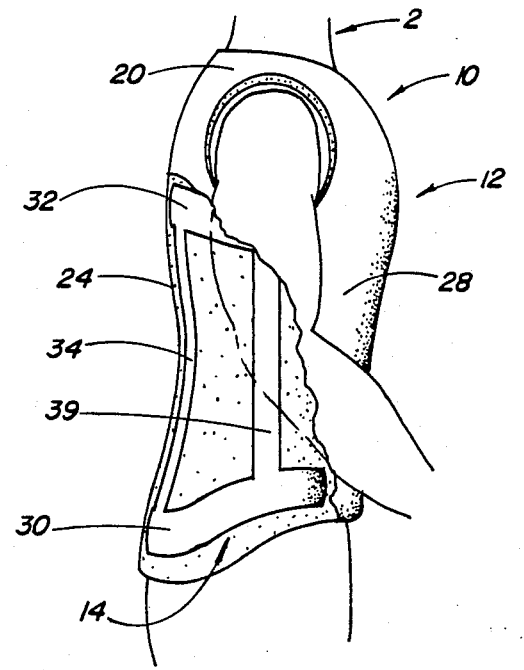
FIG. 4 is a side fragmentary view of the back supporting buoyant outfit of the present invention worn about the torso of a wearer.
Figure 5:
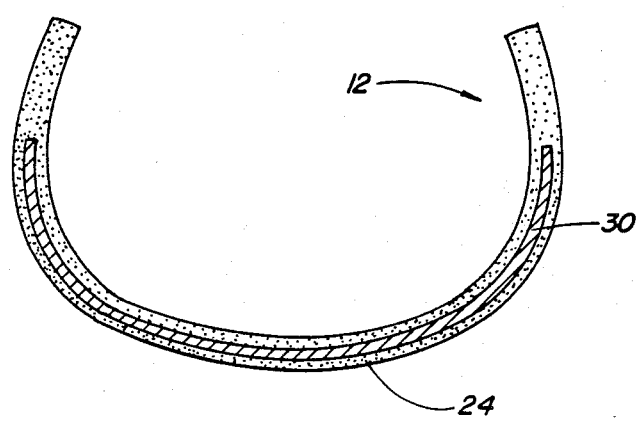
FIG. 5 is a horizontal cross-sectional view of the back supporting buoyant outfit of the present invention taken along the lines 5—5 in FIG. 3.

Imbedded within the buoyant garment 12, as illustrated in FIGS. 2 and 5, is a back or lumbar support structure 14 formed of a firm plastic or rubber material or other suitable material. The back support structure 14 includes a lower transverse member 30, an upper transverse member 32, verticle back members 34 and 36, and verticle side members 38 and 39. The lower transverse member 30 is located in the area of the wearer's lower back adjacent to the sacrum and slopes upward along both sides of the wearer 2 to the upper hip area, partially encircling the body, as shown in FIG. 4. The upper transverse member 32 is located horizontally along the upper back just below the armpits of the wearer 2 and extends from under one armpit to the area under the opposite armpit, partially encircling the wearer 2. The verticle side members 38 and 39 each extend vertically along the contour of one side of the body of the wearer 2 with one end attached to the upper transverse member 32 at a point just below the armpit and the opposite end attached to the lower transverse member 34 at the side hip area of the wearer 2. The verticle back members 34 and 36 border opposite sides of the spine of the wearer 2, as shown in FIG. 3, and follow the contour of the back of the wearer 2, as shown in FIG. 4. The verticle back members 34 and 36 are each supported by an end attached to the upper transverse member 32 and an opposite end attached to the lower transverse member 34.

A contour fit of the back supporting buoyant outfit 10 about the wearer's body is necessary for optimal back support and buoyancy for the wearer 2. Adjustment straps 40, located at the front panel 26 of the buoyant garment 12 and adjustment strap connectors 44 located at the opposite front panel 28, are used to pull and connect the back supporting buoyant outfit 10 snugly about the contour of the wearer's body, as illustrated in FIG. 1. Hence, the back support structure's position about the wearer's body is also adjusted to a proper position about the contour of the wearer's body by the adjustment straps 40 and adjustment strap connectors 44. The adjustment straps 40 and adjustment strap connectors 44 may be attached to the buoyant garment 12 or directly to the imbedded back support structure 14 for a sturdier attachment. Similarly, some extra flexibility in certain portions of the back support structure 14 would enable the back support buoyant outfit 10 to be more readily adjusted about the contour of the wearer's back. With the back supporting buoyant outfit 10 tightly about the body, the wearer 2 is provided both buoyancy and an effective back brace which hinders excessive and incorrect bending of the lower back.

In summary, the back supporting buoyant outfit 10 provides both buoyancy to the wearer 2 which helps prevent drownings and positive lumbar back support to the wearer 2 which helps prevent the danger of back injury or strain.

From the foregoing specification and discussion, it is seen that the buoyant garment 12 of the present invention is designed to encompass a substantial area of a subject's upper body, particularly that area of the back extending from the armpits downwardly to the tail bone area. Implanted and integrally formed in the buoyant garment 12 is a positive back or lumbar support structure 14. It is to be emphasized that the back or lumbar support structure 14 is integrally contained within the buoyant garment 12 itself. Preferrably the buoyant garment 12 would be constructed of a relatively pliable material while the positive back or lumbar support structure 14 implanted therein would be of a relatively rigid material. Effectively, when the back support structure 14 is tensioned around the subject's back, the positive back and lumbar and support structure 14 tends to push inwardly adjacent the subject's back and consequently imparts a back supporting function thereto.

This restricts the bending of the back, maintains the back in an upright and erect posture, and maintains the back within the confines of the back support structure 14.

The back supporting buoyant outfit 10 of the present invention has special application as a theraputic device. An individual encountering or having back problems can utilize the same to carry out an exercise program within a water environment. Beyond that, an individual having back problems may actually take part in certain water sports such as water-skiing and boating.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A positive lumbar support garment adapted to be worn about the torso of a patient for immobilizing and supporting the lumbar region of the patient comprising:
   (a) a relatively soft and pliable buoyant garment that extends around the lower torso and lumbar region of the patient and includes back, side and front areas with the front being openable;
   (b) positive lumbar support structure means implanted into the back area of the buoyant garment and extending outwardly to the side area for positively immobilizing and supporting the lumbar region of the patient;
   (c) the positive lumbar support structure including a relatively hard frame structure that as implanted extends over the lumbar region and around the lower torso of the patient where the frame acts to positively immobilize and support the lumbar region; and
   (d) means for pulling the implanted lumbar support structure firmly against the back and lumbar region of the patient and maintaining the implanted lumbar support structure in that position while the same is held about the patient's lower torso through the buoyant garment wherein the implanted lumber support structure acts to positively immobilize and support the lumbar region.

2. The positive lumber support garment of claim 1 wherein the lumbar support structure includes:
   (a) an upper generally transverse member located below the armpits of a wearer and horizontally encircling the back area of the wearer's torso;
   (b) a lower transverse member extending around the lower back area of the wearer and generally wrapping about the adjacent hip areas; and
   (c) a plurality of vertical members extending vertically along the contour of the torso and interconnected between the upper and lower transverse members.

3. The positive lumbar support garment of claim 1 wherein the back of the buoyant garment extends downward to where it extends over the lumbar region of the patient and wherein the implanted lumbar frame structure includes a lower frame portion that extends inwardly and slightly downwardly from opposite sides to where the lower portion of the implanted lumbar frame structure overlies the lumbar region of the patient.

* * * * *